United States Patent [19]

Like et al.

[11] 4,336,152

[45] Jun. 22, 1982

[54] DISINFECTANT/CLEANSER COMPOSITIONS EXHIBITING REDUCED EYE IRRITANCY POTENTIAL

[75] Inventors: Burton M. Like, East Brunswick; Dennis Smialowicz, Waldwick; Eugene Brandli, Towaco, all of N.J.

[73] Assignee: American Cyanamid Company, Stamford, Conn.

[21] Appl. No.: 280,660

[22] Filed: Jul. 6, 1981

[51] Int. Cl.$^3$ .................... C11D 1/835; C11D 3/22; C11D 3/348

[52] U.S. Cl. .................................. 252/106; 424/329; 252/139; 252/173; 252/174.17; 252/174.21; 252/528; 252/DIG. 5; 252/DIG. 14

[58] Field of Search ................ 424/329; 252/106, 139, 252/173, 174.17, 174.21, 528, DIG. 5, DIG. 14

[56] References Cited

U.S. PATENT DOCUMENTS 2,577,773  12/1951  Lambert ............................. 424/329
3,156,656  11/1964  Libby .................................. 252/106
3,402,242   9/1968  Laumann ........................... 424/329
4,013,576   3/1977  Loshaek ............................. 424/329

*Primary Examiner*—Sam Silverberg
*Attorney, Agent, or Firm*—William H. Calnan

[57] ABSTRACT

Disinfectant/cleanser compositions retaining broad spectrum germicidal activity but exhibiting significantly reduced eye irritancy potential comprise a quaternary ammonium compound, a non-ionic surfactant, d-limonene, a phosphate builder, an eye irritancy reducing compound, water, and optionally a lower aliphatic alcohol.

9 Claims, No Drawings

DISINFECTANT/CLEANSER COMPOSITIONS EXHIBITING REDUCED EYE IRRITANCY POTENTIAL

This invention relates generally to disinfectant/cleanser compositions for hard surface soil and stain removal. More particularly, it relates to such compositions which possess broad spectrum germicidal efficacy, contain d-limonene which acts as a fragrance and a soil and stain remover, and further include maltodextrin which reduces the ocular irritancy potential of the compositions. In addition to the foregoing components, the compositions also contain a quaternary ammonium compound, a non-ionic surfactant, a phosphate builder, water, and, optionally, a lower aliphatic alcohol.

Disinfectant/cleanser compositions containing d-limonene as a soil and stain remover are well known. Incorporation of phosphate builders, such as sodium tripolyphosphate and tetrapotassium pyrophosphate, into such compositions is likewise well known. The presence in these compositions of a quaternary ammonium compound and, to a lesser extent, a non-ionic surfactant imparts a broad spectrum germicidal activity thereto, i.e., the composition is effective in killing both gram positive and gram negative organisms. However, the quaternary ammonium compound has a rather irritating effect on the eye, as disclosed by the Draize Test on white albino rabbits. (See "Principles and Procedures for Evaluating the Toxicity of Household Products," National Academy of Science Publication 1138 (1977).) The surfactant also contributes to the irritancy of the composition, albeit generally to a lesser degree.

While various attempts have been made to reduce the eye irritancy of these disinfectant/cleanser compositions, such as by reducing the concentration of the quaternary ammonium compound and/or the non-ionic surfactant, none has satisfactorily done so without concommitantly impairing the germicidal efficacy of the compositions. Accordingly, it is an object of the instant invention to provide disinfectant/cleanser compositions exhibiting broad spectrum germicidal activity which have significantly reduced eye irritancy potential.

It has been discovered that the foregoing object may be achieved by incorporating into a d-limonene- and phosphate builder-containing broad spectrum germicidally active composition, an effective amount of maltodextrin which significantly mitigates the eye irritation of said composition when evaluated according to the aforementioned Draize Test.

The maltodextrin is used in the composition in an amount sufficient to significantly reduce the eye irritation potential thereof. Generally, the maltodextrin comprises about 0.1 to 5%, by weight, of the composition, with about 1 to 3%, by weight, preferred. The amount used, however, will vary depending upon, inter alia, the irritancy levels of the other ingredients in the composition. Accordingly, the optimum amount of maltodextrin to be included in a given "base" formulation will best be determined by routine experimentation.

As stated above, the quaternary ammonium compounds used in disinfectant/cleanser compositions are generally the primary irritants, the extent of the eye irritation increasing with increasing concentration. The non-ionic surfactant behaves similarly, although its contribution to irritation is generally not as great as that of the quaternary ammonium compound. However, there is apparently no synergistic irritation effect brought about by the combination of the quaternary ammonium compound and the non-ionic surfactant.

Quaternary ammonium compounds useful in the composition of the instant invention include long chain ($C_8$–$C_{12}$) dialkyldimethyl ammonium chlorides, such as dioctyldimethyl ammonium chloride and didecyldimethyl ammonium chloride, or mixtures thereof, and n-alkyl ($C_{12}$–$C_{18}$) dimethylbenzyl and n-alkyldimethylethylbenzyl ammonium chlorides. Bardac 20 (Lonza) is a preferred long chain dialkyldimethyl ammonium chloride and comprises about 25%, by weight, dioctyl-, 25% didecyl-, and 50% octyldecyldimethyl ammonium chlorides. BTC 2125 (Onyx) is a preferred n-alkyldimethylbenzyl ammonium chloride comprising about 50%, by weight, $C_{12}$–$C_{18}$ alkyldimethylbenzyl ammonium chlorides and 50% $C_{12}$–$C_{18}$ alkyldimethylethylbenzyl ammonium chlorides. The quaternary ammonium compound is generally present in the composition in an amount equal to about 3 to 10%, by weight, with about 3 to 6%, by weight, preferred.

The non-ionic surfactants used in the formulation of this invention include, but are not limited to, that class of compounds formed by condensation of an alkyl phenol, an alkyl amine, an aliphatic alcohol, or a fatty acid with sufficient ethylene oxide to produce a compound having a polyethylene chain within the molecule, i.e., a chain composed of recurring (—O—$CH_2$—$CH_2$—) groups. Many compounds of this type are known. Exemplary of this type of surfactant are those compounds produced by condensing about 5–30, preferably about 8–16, moles of ethylene oxide with one mole of (1) an alkyl phenol having about 0–15, preferably 7–10, carbon atoms in the alkyl group; (2) a alkyl amine having about 10–20, preferably 12–16, carbon atoms in the alkyl group; (3) an aliphatic alcohol having about 9–20, preferably 12–16, carbon atoms in its molecule; and (4) A fatty acid having about 10–20, preferably 12–16, carbon atoms in its molecule. Preferred non-ionic surfactants include Neodol 25-9 (Shell Chemical Co.), which is an ethoxylated mixture of normal and 2-methyl branched primary $C_{12-15}$ alcohols having about 9 moles of condensed ethylene oxide, and Triton X100 (Rohm & Haas), which is an octylphenol having about 9 moles of condensed ethylene oxide. The non-ionic surfactant typically comprises about 1 to 10%, by weight, of the composition, with about 3 to 8%, by weight, preferred.

Generally, the most germicidally efficacious compositions contain non-ionic surfactant and quaternary ammonium compound in a ratio from about 0.5:1 to 8:1. Preferably the ratio is from about 2:1 to 4:1. This is so because the presence of too much non-ionic surfactant tends to interfere with the germ killing effectiveness of the quaternary ammonium compound. However, in large part this will depend upon the mix of ingredients used. It will therefore be understood that the optimum ratio of non-ionic surfactant to quaternary ammonium compound in a given formulaton is best determined by routine experimentation.

The d-limonene which is incorporated into the composition functions as a fragrance and as a soil and stain remover. As a fragrance, its citrus scent simply imparts a pleasant odor to the composition. As a soil and stain remover, the grease cutting capability of d-limonene is well known. Typically, the d-limonene comprises about 0.25 to 6%, by weight, of the composition, with about 3 to 5%, by weight, preferred.

Also present in the composition of the present invention are conventional phosphate builders which serve, inter alia, to improve the detergent properties of the composition. Exemplary of such phosphate builders are sodium tripolyphosphate, trisodium phosphate, tetrasodium pyrophosphate and the corresponding potassium salts. The phosphate builder generally comprises about 1 to 15%, by weight, of the composition, with about 3 to 7%, by weight, preferred.

Optionally a lower aliphatic ($C_1$–$C_3$) alcohol may be incorporated into the composition, its purpose being to stablize the composition at extreme temperatures and to reduce its viscosity. When used, the alcohol is generally present in an amount from about 1 to 6% by weight, of the composition, with about 2 to 4%, by weight, preferred.

The remainder of the composition comprises water, and may contain other additives, such as dyes, UV stabilizers, and the like.

The formulations of the present invention pass the Association of Official Analytical Chemists (A.O.A.C.). Use-Dilution Test, which appears in the A.O.A.C. Methods Manual, 13th edition (1980), at a rate which gives statistical confidence at the 95% level as compared to known compositions which use a quaternary ammonium compound to provide broad spectrum germicidal activity.

The following examples are illustrative of the present invention, but are in no way to be construed as a limitation thereof. All parts and percentages are by weight unless otherwise noted.

EXAMPLE 1

A broad spectrum germicidally active disinfectant/cleanser composition having substantially reduced eye irritancy potential is prepared having the following ingredients:

|  | Percent |
| --- | --- |
| Quaternary Ammonium Compound* | 3.0 |
| Non-ionic surfactant** | 9.0 |
| d-limonene | 3.5 |
| Phosphate Builder*** | 3.5 |
| Dye (1% solution) | 0.1 |
| Maltodextrin | 1.0 |
| Water | qs to 100 |

Note:
*BTC 2125
**Triton X 100
***Sodium tripolyphosphate

EXAMPLE 2

This example illustrates the effectiveness of the mitigant of the present invention.

A control composition, containing no mitigant, was prepared having the following ingredients:

|  | Percent |
| --- | --- |
| Quaternary Ammonium Compound* | 3.5 |
| Non-ionic surfactant** | 7.0 |
| d-limonene | 4.0 |
| Ethanol (190 proof) | 3.0 |
| Phosphate Builder*** | 7.0 |
| Dye (0.5% solution) | 0.12 |
| Water | qs to 100 |

Note:
*Bardac 20
**Neodol 25-9
***Tetrapotassium pyrophosphate

A composition was also prepared containing three percent (3%) maltodextrin. The maltodextrin was added to the above control formulation, the other ingredients remaining constant except for the amount of water.

The compositions were evaluated for eye irritation using the Draize Test. (See the aforementioned NAS Publication 1138). One-tenth of a milliliter of each composition was instilled into the right eye of each of three (3) white albino rabbits, the left eye acting as the control. The rabbits were observed for eye irritation over a 14 day period. The Draize Test employs a scoring system having a maximum score of 110 per rabbit (indicating the most severe damage). The scoring system assesses damage to: the cornea (opacity and area of corneal involvement)—maximum score of 80 per rabbit; the iris—maximum score of 10 per rabbit; and the conjunctivae (redness, chemosis and discharge)—maximum score of 20 per rabbit. The results of the test are set forth in Table I below, wherein the scores reported are the total for the three (3) rabbits after 14 days. A total score for the 3 rabbits after 14 days of less than 20 was considered a "passing score" for purposes hereof, in that a score of less than 20 would indicate that the composition was substantially less irritating than the control composition.

TABLE I

Draize Test (Eye Irritation) Scores for the Composition Containing The Eye Irritation Mitigant Of The Present Invention

| Mitigant | Total Score (3 Rabbits) |
| --- | --- |
| Control | 74 |
| Maltodextrin | 2 |

The test results demonstrate that the mitigant of the instant invention significantly reduced the eye irritation of the control formulation.

EXAMPLE 3

Several other reported irritation mitigants were separately incorporated into the control formulation of Example 2 in the manner in which the mitigant of this invention was so incorporated as set forth in Example 2, and the Draize Test results (the test being conducted as outlined in Example 2) of the resulting compositions are presented in Table II.

TABLE II

Draize Test (Eye Irritation) Scores for Compositions Containing Various Other Irritation Mitigants

| Mitigant | Total Score (3 Rabbits) |
| --- | --- |
| Control | 74 |
| Citric acid (1.5%) | 260 |
| Ascorbic Acid (1%) | 113 |
| 1,6-hexylene glycol (2%) | 187 |
| Polyvinyl pyrrolidone (3%) | 144 |
| Sucrose (3%) | 160 |
| Collagen (3%) | 114 |
| Aloin (1%) | 135 |
| Mannitol (3%) | 102 |
| Lanolin (3%) | 158 |
| Imidazole (3%) | 182 |
| Vitamin A (0.3%) | 116 |
| Stearyl dimethyl amine oxide (3%) | 126 |
| Lauryl dimethyl amine oxide (3%) | 191 |
| White mineral oil (0.6%) | 80 |
| Allantoin (1%) | 57 |
| Azulene (0.125%) | 32 |

As can be seen from Table II, other reported irritancy mitigants did not reduce eye irritation in the rabbits to the extent the mitigant of the instant invention did. In fact, in many cases the supposed mitigants actually increased eye irritation.

What is claimed is:

1. A disinfectant/cleanser composition having broad spectrum germicidal activity and exhibiting reduced eye irritancy potential which comprises:
   (a) a quaternary ammonium compound;
   (b) a non-ionic surfactant;
   (c) d-limonene;
   (d) an eye irritancy reducing effective amount of maltodextrin
   (e) a phosphate builder; and
   (f) water.

2. The composition of claim 1 further comprising a lower aliphatic alcohol.

3. The composition of claim 2 wherein the lower aliphatic alcohol is selected from the group consisting of ethanol, propanol and isopropanol.

4. The composition of claim 2 wherein the quaternary ammonium compound is selected from the group consisting of dialkyl ($C_8$–$C_{12}$) dimethyl ammonium chlorides, n-alkyl ($C_{12}$–$C_{18}$) dimethylbenzyl ammonium chlorides, and n-alkyl ($C_{12}$–$C_{18}$) dimethylethylbenzyl ammonium chlorides; the non-ionic surfactant is selected from the group consisting of condensation products of about 5–30 moles of ethylene oxide with one mole of a compound selected from the group consisting of an alkyl phenol having about 0–15 carbon atoms in the alkyl group, an alkyl amine having about 10–20 carbon atoms in the alkyl group, an aliphatic alcohol having about 9–20 carbon atoms and a fatty acid having about 10–20 carbon atoms; and the lower aliphatic alcohol is selected from the group consisting of ethanol, propanol and isopropanol.

5. The composition of claim 1 or claim 2 comprising about 3 to 10%, by weight, of the quaternary ammonium compound, about 1 to 10%, by weight, of the non-ionic surfactant, about 0.25 to 6%, by weight, of the d-limonene, about 0 to 6% by weight, of the lower aliphatic alcohol, about 1 to 15%, by weight, of the phosphate builder, and about 0.1 to 5%, by weight, of maltodextrin.

6. The composition of claim 4 comprising about 3 to 6%, by weight, of the quaternary ammonium compound, about 3 to 8%, by weight, of the non-ionic surfactant, about 3 to 5%, by weight, of the d-limonene, about 2 to 4%, by weight, of the lower aliphatic alcohol, about 3 to 7%, be weight, of the phosphate builder, and about 1 to 3%, by weight of maltodextrin.

7. The composition of claim 2 or claim 6 wherein the quaternary ammonium compound is a mixture of about 25%, by weight, dioctyl-, 25% didecyl- and 50% octyldecyldimethyl ammonium chloride, the non-ionic surfactant is an ethoxylated mixture of normal and 2-methyl branched primary $C_{12}$–$C_{15}$ alcohols having about 9 moles of condensed ethylene oxide, the phosphate builder is tetrapotassium pyrophosphate, and the lower aliphatic alcohol is ethanol.

8. The composition of claim 1, claim 2, claim 4 of claim 6 wherein the ratio of the non-ionic surfactant to the quaternary ammonium compound is about 0.5 to 8:1.

9. The composition of claim 8, wherein the ratio of the non-ionic surfactant to the quaternary ammonium compound is about 2 to 4:1.

* * * * *